United States Patent
Takagi et al.

(10) Patent No.: US 6,717,145 B1
(45) Date of Patent: Apr. 6, 2004

(54) MAPPING ELECTRON MICROSCOPES EXHIBITING IMPROVED IMAGING OF SPECIMEN HAVING CHARGEABLE BODIES

(75) Inventors: Toru Takagi, Kawasaki (JP); Naoto Kihara, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/583,001

(22) Filed: May 26, 2000

(30) Foreign Application Priority Data

May 27, 1999 (JP) .......................................... 11-147430

(51) Int. Cl.⁷ .......................... G01N 23/00; A61N 5/00; G21K 5/00; G21K 5/10
(52) U.S. Cl. ...................... 250/311; 250/306; 250/307; 250/310; 250/397; 250/492.1; 250/492.22; 250/492.3
(58) Field of Search ................................ 250/310, 311, 250/306, 315.3, 580, 582, 492.1, 492.22, 492.3, 307, 397

(56) References Cited

U.S. PATENT DOCUMENTS

| | | | | |
|---|---|---|---|---|
| 3,917,946 A | * | 11/1975 | van Oostrum | 250/307 |
| 4,785,182 A | * | 11/1988 | Mancuso et al. | 250/310 |
| 4,896,036 A | * | 1/1990 | Rose et al. | 250/310 |
| 4,954,705 A | * | 9/1990 | Brunner et al. | 250/310 |
| 4,978,855 A | * | 12/1990 | Liebl et al. | 250/310 |
| 5,004,918 A | * | 4/1991 | Tsuno et al. | 250/311 |
| 5,451,783 A | * | 9/1995 | Coxon et al. | 250/305 |
| 5,892,224 A | * | 4/1999 | Nakasuji | 250/310 |
| 5,981,947 A | * | 11/1999 | Nakasuji et al. | 250/310 |
| 6,011,262 A | * | 1/2000 | Hamashima et al. | 250/310 |
| 6,232,787 B1 | * | 5/2001 | Lo et al. | 324/751 |
| 6,259,094 B1 | * | 7/2001 | Nagai et al. | 250/310 |
| 6,344,750 B1 | * | 2/2002 | Lo et al. | 324/751 |
| 6,365,896 B1 | * | 4/2002 | van der Mast | 250/310 |
| 6,365,897 B1 | * | 4/2002 | Hamashima et al. | 250/310 |

FOREIGN PATENT DOCUMENTS

JP 2810797 7/1998

* cited by examiner

Primary Examiner—John R. Lee
Assistant Examiner—Mary El-Shammaa
(74) Attorney, Agent, or Firm—Klarquist Sparkman, LLP

(57) ABSTRACT

Mapping electron microscopes are disclosed in which the amount of charging of the specimen is controlled to between a minimum amount needed to view an image and a maximum amount beyond which a viewable image cannot be obtained that has low distortion or that does not result in specimen damage. Multiple irradiation-electron beams, or multiple segments of a single irradiation-electron beam, are directed to a specimen surface. The irradiation beams (or segments) are decelerated by a retarding voltage applied by a cathode lens and are incident on the specimen surface. The respective current and incident energy of each irradiation beam (or segment thereof) are controlled independently to a predetermined relationship so as to impart predetermined amounts of charging to different insulator regions of the specimen.

17 Claims, 4 Drawing Sheets

MAPPING ELECTRON MICROSCOPES EXHIBITING IMPROVED IMAGING OF SPECIMEN HAVING CHARGEABLE BODIES

FIELD OF THE INVENTION

This invention pertains to mapping electron microscopes and related electron-optical systems with which it is possible to view a specimen surface in two dimensions.

BACKGROUND OF THE INVENTION

A scanning electron microscope (SEM) generally is used for examining the surface of a specimen, such as the product of a step in a process for manufacturing semiconductor integrated circuits, especially to ascertain the presence of surficial defects. In view of the fact that an electron beam is an exemplary charged particle beam, investigations have been made into the use of other charged particle beams (such as a focused ion beam) for similar applications.

Since principles generally applicable to an electron beam are applicable to an ion beam, the discussion below is made in the context of an electron-beam system. However, in view of the above, it will be understood that the invention is not limited to electron-beam systems.

In an SEM, as is known generally, an electron beam is irradiated onto a point on the surface of the specimen being observed. Impingement of the electron beam on the specimen surface causes the surface to emit secondary electrons. The secondary electrons are accelerated away from the surface, collected, and quantified by a suitable detector. To image a region on the sample, the electron beam simply is scanned in two dimensions in a raster manner. Secondary electrons generated at each irradiation point in the scan are collected and quantified. The data collected by the detector are processed to form an image that is displayed on a screen (CRT) or the like.

A main disadvantage of conventional SEMs is the long period of time required for obtaining an image of the surface being observed. The time is related to the need to scan a point-focused electron beam two-dimensionally over the observed surface. As a result, "mapping electron microscopes" are being investigated for use, as a possible alternative to SEMs, in examining semiconductor wafers and chips and in other applications in which high speed is required. This is because a mapping electron microscope offers prospects of simultaneously viewing an entire region of the target surface in two dimensions. To such end, a mapping electron microscope utilizes an electron-optical system (i.e., a system comprising a 2-dimensional projection-electron lens) to direct the electron beam onto an area of the sample surface that is larger than a point. Unfortunately, various technical problems remain unresolved with mapping electron microscopes.

An important technical problem concerns electrostatic charging of the specimen surface that is being observed. Charging can occur whenever the specimen has an insulator or floating conductor. During charging, the irradiated area acquires a positive or negative electrostatic charge whenever the number (quantity) of the electrons irradiating the specimen is not equal to the number (quantity) of electrons emitted from the irradiated surface as secondary electrons and the like. Whenever charging occurs, the observed surface of the specimen is not in a desired equipotential condition; in fact, the localized potentials within the observed field can differ to such an extent (due to localized accumulations of electrostatic charges) that imaging of certain regions is impossible.

In a mapping electron microscope, low-energy electrons, especially secondary electrons and the like, are accelerated and magnified to high magnification and projected by an electrostatic lens onto an imaging surface (e.g., the surface of a detector). The energy band of such electrons that can be imaged is narrow due to defocusing (on-axis chromatic aberrations). Also, energy uniformity across the entire imaging field is difficult to sustain. Serious problems can arise if the distribution of electrical potential varies greatly over the specimen surface because the image in the vicinity of such variations is distorted or cannot be formed at all, making accurate observation impossible. In addition, the specimen itself may be damaged if it becomes charged sufficiently greatly to cause an electrostatic discharge or insulation breakdown.

The occurrence of charging is determined at least in part by the "secondary-electron production efficiency." The secondary-electron production (SEP) efficiency is the current of produced secondary electrons divided by the beam current of charged particles in the beam irradiating the specimen. If the SEP efficiency is greater than unity (1), then the specimen acquires a positive electrostatic charge; if the SEP efficiency is less than unity, then the specimen acquires a negative electrostatic charge. Hence, to avoid the problems summarized above, it would be advantageous if specimen irradiation could be performed (especially with respect to insulators and floating conductors) in a manner by which the SEP efficiency is maintained as close to unity as possible.

However, a typical specimen (especially a patterned semiconductor wafer or chip) typically includes multiple types of insulators and floating conductors each having a different respective SEP efficiency. With such specimens, it is conventionally extremely difficult to observe the specimen by mapping electron microscopy without causing, unacceptable levels of localized charging. Many specimens simply cannot be imaged at all without intentionally charging them at least to a certain extent (e.g., to obtain a potential-contrast image). In such instances, it is difficult or impossible to control the extent of localized or general charging of the specimen.

SUMMARY OF THE INVENTION

The shortcomings of the prior art as summarized above are solved by mapping electron microscopes according to the present invention in which the degree of localized charging of the specimen is controlled, especially with respect to insulators and floating conductors. Hence, the charging is maintained between a minimum needed for producing a viewable image and a maximum beyond which a viewable image is not obtainable with sufficiently low distortion or without damaging the specimen.

This invention provides, inter alia, mapping electron microscopes comprising an irradiation-optical system that irradiates the observed surface of a specimen with electrons from an electron source. The mapping electron microscopes also comprise an electron-imaging optical system that collects imaging electrons-emitted from the irradiated surface of the specimen and directs them onto an image-pickup surface ("detector").

One embodiment of such a mapping electron microscope comprises an irradiation-optical system, an imaging-electron detector, and a projection-optical system. The irradiation-optical system is situated and configured to irradiate a surface of a specimen with charged particles produced by a charged-particle source, so as to cause the specimen surface to emit imaging electrons. The imaging-electron detector comprises a detection surface. The projection-optical system is situated and configured to direct the imaging electrons in an image-forming way onto the detection surface. The irradiation-optical system is further configured to produce the beam controllably having a characteristic such that localized changes in potential due to charging by the beam at one or more regions of the specimen surface, when irradiated by the beam from the irradiation optical system, are within respective predetermined ranges in which an image of each such respective region can be obtained. The imaging optical system can be further configured such that each of multiple regions on the specimen surface is irradiated so as to acquire a respective change of surface potential ($U_s$) that is greater than a respective minimum change of surface potential ($U_{min}$) needed to produce a viewable image and a respective maximum change of surface potential ($U_{max}$) beyond which a viewable image cannot be obtained. The mapping electron microscope can include a Wien filter situated and configured to direct the beam of charged particles from the irradiation-optical system to the specimen surface.

Using a Wien filter allows for perpendicular irradiation of the specimen, which facilitates uniform irradiation of the specimen compared to angled irradiation. Koehler illumination conditions can be created by placing an aperture between the Wien filter and the specimen, and aligning the focal point of a cathode lens (located between the aperture and the specimen) with the aperture position.

In another embodiment of a mapping electron microscope according to the invention, the irradiation-optical system is situated and configured to irradiate a surface of a specimen simultaneously with electrons produced by multiple electron sources. The electrons from each source have a respective current and respective incident energy that are controlled independently at each source. The electrons incident on the specimen surface cause the specimen surface to emit imaging electrons. The mapping electron microscope also includes an imaging-electron detector and a projection-optical system that is situated and configured to route the imaging electrons in an image-forming way to the detection surface of the imaging detector. In this embodiment, the irradiation-optical system can comprise the multiple electron sources.

For example, the irradiation-optical system can comprise a separate respective irradiation column corresponding to each electron source. In such a configuration, each electron source produces a respective irradiation beam. The irradiation-optical system can include a Wien filter. The Wien filter is situated and configured to receive each irradiation beam from a respective deflection angle relative to an optical axis, and to direct each respective irradiation beam along the optical axis to the specimen surface. As another example, the irradiation-optical system can comprise a first and a second electron source. The first electron source produces a first irradiation beam at an angle $\theta_1$ relative to the optical axis, and the second electron source produces a second irradiation beam at an angle $\theta_2$ relative to the optical axis. The respective angles $\theta_1$, $\theta_2$ are established according to:

$$L=(\sin \theta_1/eB)(2m)^{1/2}V_{11}/[(V_{11})^{1/2}+(V_{ret})^{1/2}]$$

$$L=(\sin \theta_2/eB)(2m)^{1/2}V_{12}/[(V_{12})^{1/2}+(V_{ret})^{1/2}]$$

wherein B is a magnetic field produced by the Wien filter fulfilling a Wien condition with respect to secondary electrons accelerated from the specimen surface at a retarding voltage ($V_{ret}$) formed by the surface potential, e is the absolute value of the electron charge, m is the mass of an electron, $V_{11}=V_1+V_{ret}$ wherein $V_1$ is an incident energy of the first irradiation beam, and $V_{12}=V_2+V_{ret}$ wherein $V_2$ is an incident energy of the second irradiation beam. Furthermore, the angles $\theta_1$, $\theta_1$, $\theta_2$ can satisfy the following:

$$\sin \theta_1/\sin \theta_2 = V_{12}[(V_{11})^{1/2}+(V_{ret})^{1/2}]/\{V_{11}[(V_{12})^{1/2}+(V_{ret})^{1/2}]\}$$

Further by way of example, each electron source can be configured to produce a respective irradiation beam, and the irradiation-optical system can comprise a respective Wien filter for each irradiation beam. In this configuration, each Wien filter is situated and configured to receive the respective irradiation beam from a respective angle relative to an optical axis, and to direct the respective irradiation beam along the optical axis to the specimen surface. With this embodiment, the multiple electron sources facilitate keeping changes in surface potential of the specimen due to charging of various insulator bodies or floating conductors within respective target values.

In another embodiment of a mapping electron microscope according to the invention, an electron source is configured to produce a beam of irradiation electrons. The beam has a first segment containing irradiation electrons at a first beam current and incident energy, and a second segment containing irradiation electrons at a second beam current and incident energy. The second segment is in temporal series with the first segment. The embodiment also includes an irradiation-optical system situated and configured to irradiate a surface of a specimen with the beam of irradiation electrons produced by the electron source. The irradiation-optical system is further configured to separate the second segment temporally from the first segment and to control the beam current and incident energy of at least one segment as incident on the specimen surface. The embodiment also includes an imaging-electron detector comprising a detection surface, and a projection-optical system. The projection-optical system is situated and configured to route the imaging electrons in an image-forming way to the detection surface of the imaging detector. This mapping electron microscope can include a Wien filter situated and configured to direct a beam of charged particles from the irradiation-optical system to the specimen surface.

Hence, in this embodiment, specimen irradiation is performed by dividing the current and incident energy from at least one electron source into temporal (time) segments. The achieved result is the same as if there were multiple electron sources each producing a respective irradiation beam having a respective beam current and incident energy. This is because charging of locations on the specimen surface is chronologically and spatially overlapping.

The detector can include an imaging-electron converter and a photoelectric converter, such as a CCD. The detector receives the imaging electrons and converts them to a corresponding electrical signal. The charge per each temporal cycle of irradiation is accumulated by the CCD. Respective outputs from the CCD for the different irradiation cycles are output to produce an image.

Desirably, irradiation is performed under uniform irradiation conditions within the irradiation field. This produces a clear image without lightening or darkening of the image based on localized charging or irradiation irregularities within the field.

The foregoing and additional features and advantages of the invention will be more readily apparent from the following detailed description, which proceeds with reference to the accompanying drawings.

DETAILED DESCRIPTION

General Considerations

As noted above, a typical specimen for mapping electron microscopy includes multiple individual insulator bodies and conductors. The respective change of surface potential ($U_s$) of each such body or region desirably is controlled so that the potential is between a minimum change in surface potential ($U_{min}$) needed to produce a viewable image and a maximum change in surface potential ($U_{max}$) beyond which a viewable image cannot be obtained (due, for example, to the image having excess distortion or the specimen being damaged by electrostatic discharge). Also, irradiation of the specimen desirably is performed under uniform illumination conditions within the imaging field to facilitate obtaining a clear image without localized lightening or darkening from respective localized charging or irradiation irregularities within the field.

As used herein, "imaging electrons" are electrons emitted from the specimen or other surface due to irradiation by a charged particle beam. Imaging electrons include, for example, reflected electrons, secondary electrons, and backscattered electrons.

The changes of surface potentials noted above desirably have the following relationship for optimal imaging:

$$U_{min} < U_s < U_{max} \quad (1)$$

The efficiency with which imaging electrons are emitted from an irradiated region of the specimen is a function of the energy of the irradiating electrons (or other charged particles), the substance and structure of the specimen, the imaging environment, and other factors.

Most substances used in semiconductor-fabrication processes have a secondary-electron production (SEP) efficiency greater than unity (1) in irradiating-electron fields of 100 eV to 1 KeV, but less than unity in fields outside this range. Also, whenever a floating conductor or insulator is irradiated for a period of time, the conductor or insulator accumulates charge and exhibits a corresponding change in potential over time. If the specimen has only one type of floating conductor or insulator, and if the specimen is uniform, then the specimen can be irradiated readily with a single beam having an energy that will yield a SEP efficacy of unity. However, if the specimen comprises multiple types of substances (which is the case with most semiconductor wafers and chips), then the irradiation energy that will yield a SEP efficiency of unity typically will differ for each of the constituent substances. Under such conditions, optimal imaging of all regions of the specimen surface usually cannot be performed using a single beam having a single energy level. Either multiple beams are required (each having a respective energy level), or a single beam with multiple energy levels is required.

Figure 1:
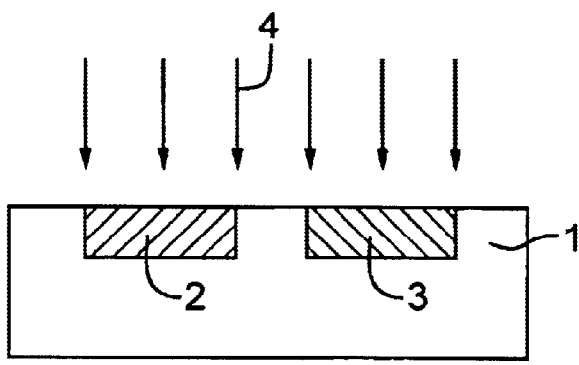
FIG. 1 is a schematic elevational section showing exemplary insulator bodies in a specimen irradiated with a single electron beam for mapping electron microscopy.

For example, consider a specimen having an elevational sectional profile as shown in FIG. 1, in which regions 2, 3 are respective insulator bodies A and B in a silicon substrate 1. The substrate 1 is electrically conductive whereas the insulator bodies A, B are not. The top surface of the specimen is irradiated (arrows 4) by incident electrons within an illumination field with the intention of producing an image of the specimen surface. Because the specimen in this example has a planarized top surface (as achieved by a suitable technique such as CMP), image contrast generally will be too low for obtaining a good image by optical microscopy or even by edge-emphasized SEM microscopy.

Figure 2A:
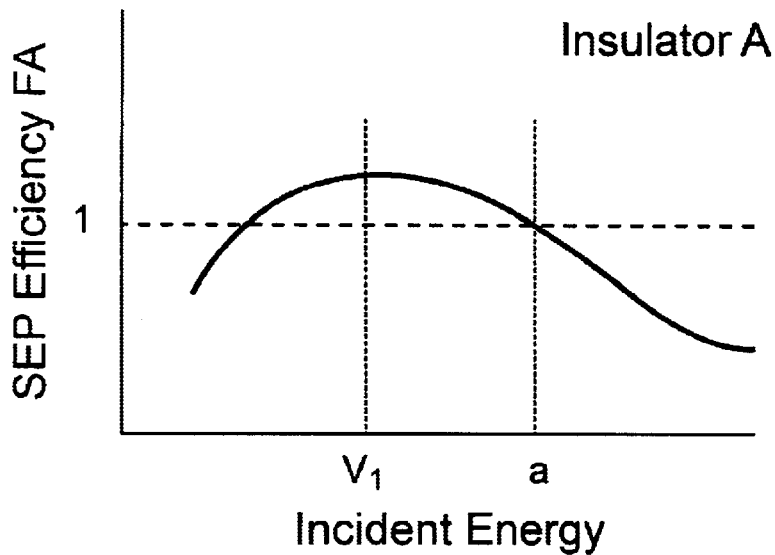
FIGS. 2(a)–2(b) are respective graphs of representative relationships between incident energy (of an electron beam) and secondary-electron production efficiency of respective insulator bodies such as shown in FIG. 1.
Figure 2B:
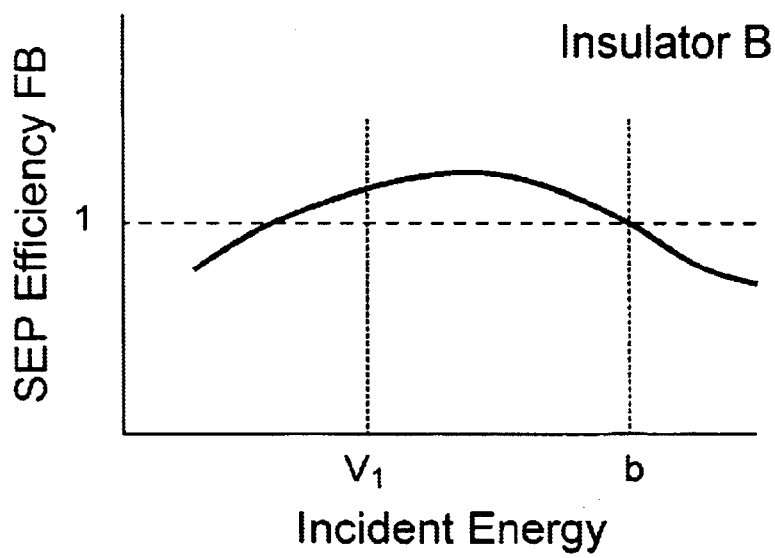

Upon illuminating the FIG. 1 specimen with electrons 4 having an incident energy of $V_1$ localized charging occurs that tends to change the incident energy of electrons on regions undergoing localized charging. To the extent that there is no leakage current, the incident energy on the insulator bodies A, B shifts from the initial value of $V_1$ to respective levels "a" and "b" as shown in FIGS. 2(a)–2(b), respectively. The levels "a" and "b" correspond to respective SEP efficiencies of the respective insulator bodies A and B at irradiation equilibrium. As a result, the change of (shift in) the charging potential of the insulator bodies A ($U_{s/A}$) and the change of (shift in) the charging potential of the insulator body B ($U_{s/B}$) increases by (a–$V_1$) and (b–$V_1$), respectively.

The shifts in charging potentials $U_{s/A}$ and $U_{s/B}$ simultaneously may fulfill the following two inequalities:

$$U_{min} < U_{s/A} < U_{max} \quad (2)$$

$$U_{min} < U_{s/B} < U_{max} \quad (3)$$

(Note that, above, $U_{min}$ and $U_{max}$ are the same for each body A and B.) However, there generally are many instances in which these conditions cannot be achieved, even if the respective levels of $V_1$ are changed in FIGS. 2(a) and 2(b).

Figure 3:
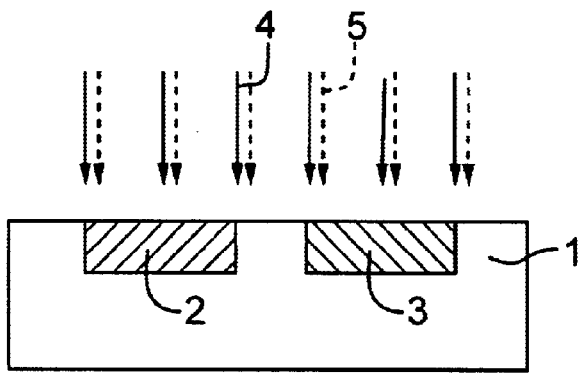
FIG. 3 is a schematic elevational section showing exemplary insulator bodies in a specimen irradiated with multiple electron beams for mapping electron microscopy.
Figure 4A:
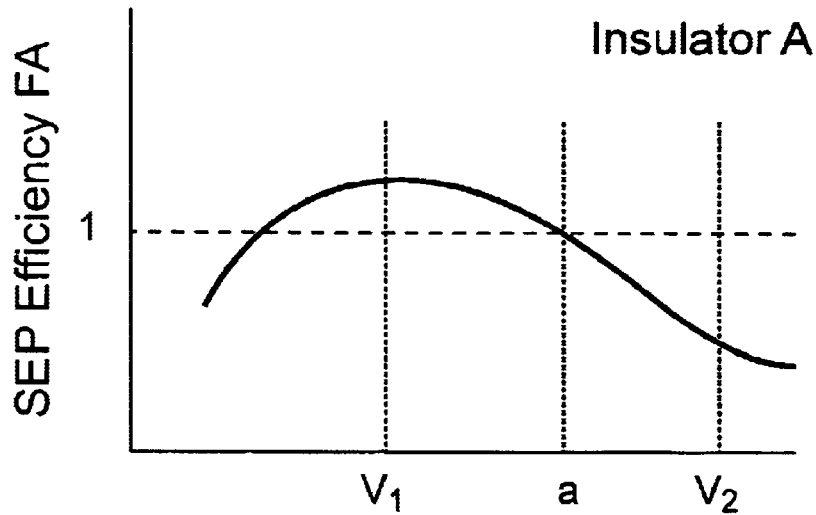
FIGS. 4(a)–4(b) are respective graphs of representative relationships between incident energy (of an electron beam) and secondary-electron production efficiency of respective insulator bodies such as shown in FIG. 3.
Figure 4B:
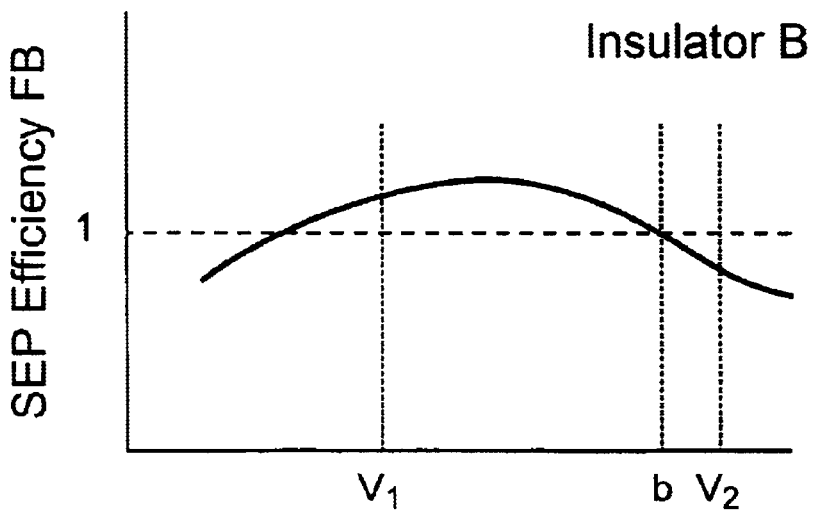

Now, assume that the specimen is irradiated simultaneously with electrons 4 having an incident energy of $V_1$ and electrons 5 having an incident energy of $V_2$, as shown in FIG. 3. $V_1$ and $V_2$ are selected so as to be situated on opposite sides of the equilibrium points a and b of the respective insulator bodies A and B, as shown in FIGS. 4(a) and 4(b), respectively. The respective shifts in charging potential $U_{s/A}$, $U_{s/B}$ of the insulator bodies A and B, irradiated with the electrons of two different energies $V_1$, $V_2$, are found as follows.

The SEP efficiency functions for the insulator bodies A and B, as functions of the irradiation electron energy V, are denoted FA(V) and FB(V), respectively. The respective irradiation-electron beam currents at the specimen surface of the beams having respective incident energies of $V_1$ and $V_2$ are $I_1$ and $I_2$, respectively. The respective secondary-electron beam currents emitted from the surfaces of the respective insulators A and B when irradiated at the respective incident energies V and $V_2$ are expressed as:

from A: $I_1 \cdot FA(V_1) + I_2 \cdot FA(V_2)$ (4)

from B: $I_1 \cdot FB(V_1) + I_2 \cdot FB(V_2)$ (5)

As can be seen, the respective sums indicated in Expressions (4) and (5) generally are not the same as the sum of the incident irradiation-beam currents:

$$I_1+I_2 \quad (6)$$

Rather, in Expressions 4 and 5, each of the $I_1$ and $I_2$ terms is factored by the respective SEP efficiency (FA) function. As a result, charging of the respective insulator bodies occurs until equilibrium is reached. At equilibrium, the incident energy $V_1$ is shifted to $V_1+U$ by the charge-up potential U, and the respective shifts in surface potential $U_{s/A}$, $U_{s/B}$ reach the following respective steady-state conditions:

$$\text{for } A: I_1+I_2=I_1 \cdot FA(V_1+U_{s/A})+I_2 \cdot FA(V_2+U_{s/A}) \quad (7)$$

$$\text{for } B: I_1+I_2=I_1 \cdot FB(V_1+U_{s/B})+I_2 \cdot FB(V_2+U_{s/B}) \quad (8)$$

If the variable $\alpha$ is denoted as follows:

$$\alpha=I_1/(I_1+I_2) \quad (9)$$

then Equations (7) and (8) can be written respectively as:

$$\text{for } A: 1=\alpha \cdot FA(V_1+U_{s/A})+(1-\alpha) \cdot FA(V_2+U_{s/A}) \quad (10)$$

$$\text{for } B: 1=\alpha \cdot FB(V_1+U_{s/B})+(1-\alpha) \cdot FB(V_2+U_{s/B}) \quad (11)$$

If $U_{s/A}$ and $U_{s/B}$ and one of $\alpha$, $V_1$, and $V_2$ are established at specific values that fulfill Expressions (2) and (3), then the remaining two variables can be determined so that both Equations (10) and (11) are satisfied, thereby allowing the specimen to be imaged with good results. Moreover, by changing the total irradiation current density, illumination can be accomplished under even better irradiation conditions because the image is brightened.

As can be ascertained from the foregoing, if $\alpha$, $V_1$, and $V_2$ in Equations (10) and (11) are all found as variables, then the respective values can be applied to up to three types of insulators. (For example, for a third insulator FC(V) experiencing a shift in charging potential $U_{s/C}$, $1=\alpha \cdot FC(V_1+U_{s/C})+(1-\alpha) \cdot FC(V_2+U_{s/C})$.) Since the number of new variables increases by two (i.e., an additional incident-energy (V) term and an additional beam-current (I) term is added) for each additional beam supplying another level of irradiation electron energy, the number of types of insulators to which these principles can be applied also increases by two under such conditions. (I.e., each beam has two variables V and I. Simultaneous equations involving these variables have two solutions.)

Hence, the irradiation-optical system can be configured such that the specimen being observed is irradiated simultaneously by illumination from multiple electron sources each having a respective current (I) and incident energy (V) that are controlled independently, as described above. The respective currents and incident energies can be established to maintain the changes in the surface potential due to charging within respective target values for each insulator or floating conductor. This allows the surface potential ($U_s$) due to charging to be controlled for each insulator and/or floating conductor so that the surface potential is between a minimum amount ($U_{min}$) needed to view an image and a maximum amount ($U_{max}$) beyond which a viewing image cannot be obtained with low distortion and/or without damaging the specimen itself.

The invention is further described below in the context of representative embodiments. However, it will be understood that the invention is not limited to these embodiments.

Representative Embodiment 1

Figure 5:
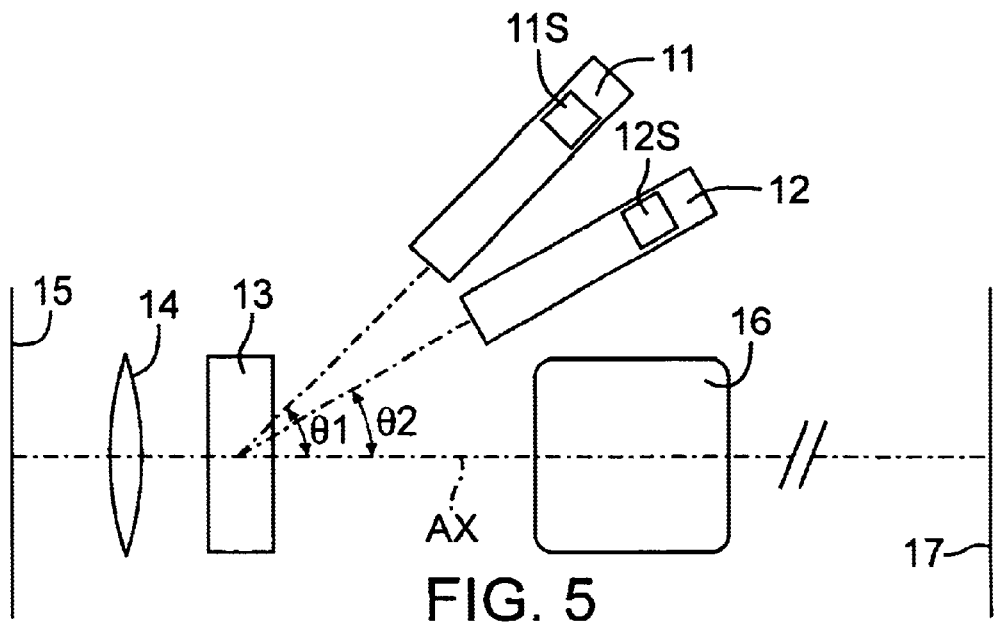
FIG. 5 is a schematic optical diagram of a mapping electron microscope according to a first representative embodiment of the invention.

This embodiment, depicted in FIG. 5, comprises irradiation-beam columns 11, 12, a Wien filter (ExB) 13, a cathode lens 14, a projection-optical system 16, and a detection surface 17 (e.g., surface of a suitable detector of secondary electrons). The specimen surface is denoted by the numeral 15.

The irradiation columns 11, 12 accelerate electrons from respective electron sources 11S, 12S and form the electrons into respective beams of predetermined respective transverse profile and area. The irradiation column 11 is situated at a respective angle $\theta_1$ to the optical axis AX, and the irradiation column 12 is situated at a respective angle $\theta_2$ to the optical axis AX. The respective irradiation beams propagate to the optical center of the Wien filter 13. Each irradiation beam is deflected by the Wien filter 13 to propagate along the axis AX toward the specimen surface 15. Hence, the irradiation beams are incident perpendicularly to the specimen surface 15. The irradiating electrons in the irradiating beams are decelerated by a retarding voltage applied by the cathode lens 14 and are incident onto a predetermined area of the specimen surface 15.

An aperture (not shown) desirably is situated between the Wien filter 13 and the cathode lens 14. By locating the aperture at the focal point of the cathode lens 14, the aperture serves to Koehler-irradiate the specimen surface 15.

In the following discussion, the irradiation beams entering the Wien filter 13 from the irradiation columns 11, 12 have respective energies of $V_{11}$ and $V_{12}$, and respective incident energies $V_1$ and $V_2$. The potential energy imparted to the respective irradiation beams by the retarding voltage imposed by the cathode lens 14 is denoted $V_{ret}$. The potential energy $V_{ret}$ can be positive or negative relative to the specimen surface 15, but normally is positive. The energies $V_{11}$ and $V_{12}$ are expressed as, respectively:

$$V_{11}=V_1+V_{ret} \quad (12)$$

$$V_{12}=V_2+V_{ret} \quad (13)$$

The respective beam-current values of the irradiation beams from the respective columns 11, 12 are denoted $I_1$ and $I_2$, which are related to $V_1$, $V_2$, and $\alpha(=I_1/(I_1+I_2))$ as set forth in Equations (10) and (11).

The respective deflection angles $\theta_1$ and $\theta_2$ of the irradiation beams are established simultaneously according to the following:

$$L=(\sin \theta_1/eB)(2m)^{1/2}V_{11}/[(V_{11})^{1/2}+(V_{ret})^{1/2}] \quad (14)$$

$$L=(\sin \theta_1/eB)(2m)^{1/2}V_{12}/[(V_{12})^{1/2}+(V_{ret})^{1/2}] \quad (15)$$

within a magnetic field B that fulfills Wien conditions with respect to the secondary electrons accelerated at a retarding voltage of $V_{ret}$, wherein "L" is the nominal thickness of the Wien filter 13, "e" is the absolute value of the charge of an electron, and "m" is the mass of an electron. At known respective energies V11, V12, the deflection angles $\theta_1$, $\theta_2$ can be set to any value that satisfies the relation:

$$\sin \theta_1/\sin \theta_2=V_{12}[(V_{11})^{1/2}+(V_{ret})^{1/2}]/\{V_{11}[(V_{12})^{1/2}+(V_{ret})^{1/2}]\} \quad (16)$$

If the deflection angles $\theta_1$, $\theta_2$ are set accordingly, then the incident energies can be selected in satisfaction of Equation (16). It is possible to vary the respective irradiation-current densities randomly by changing the parameters of the respective electron sources 11S, 12S and irradiation columns 11, 12.

Representative Embodiment 2

Figure 6:
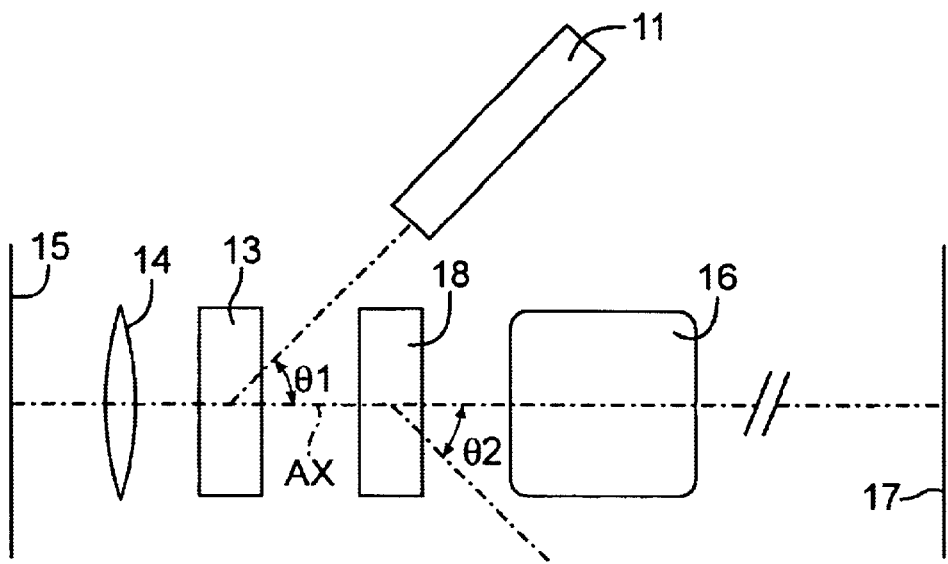
FIG. 6 is a schematic optical diagram of a mapping electron microscope according to a second representative embodiment of the invention.

This embodiment is shown in FIG. 6, and includes a second Wien filter 18. All other components in this embodiment are similar to corresponding components in the FIG. 5 embodiment and have the same respective reference numerals. Irradiation electrons from the irradiation column 11 and irradiation electrons from the irradiation column 12 enter the separate Wien filters 13, 18, respectively. Consequently, in this embodiment, the magnetic fields B in Equations (14) and (15) are independent. This configuration makes it possible to change the electron energies of the various irradiation systems independently. The respective irradiation-current densities can be varied randomly by changing the parameters of the respective electron guns and irradiation columns.

Representative Embodiment 3

Figure 7:
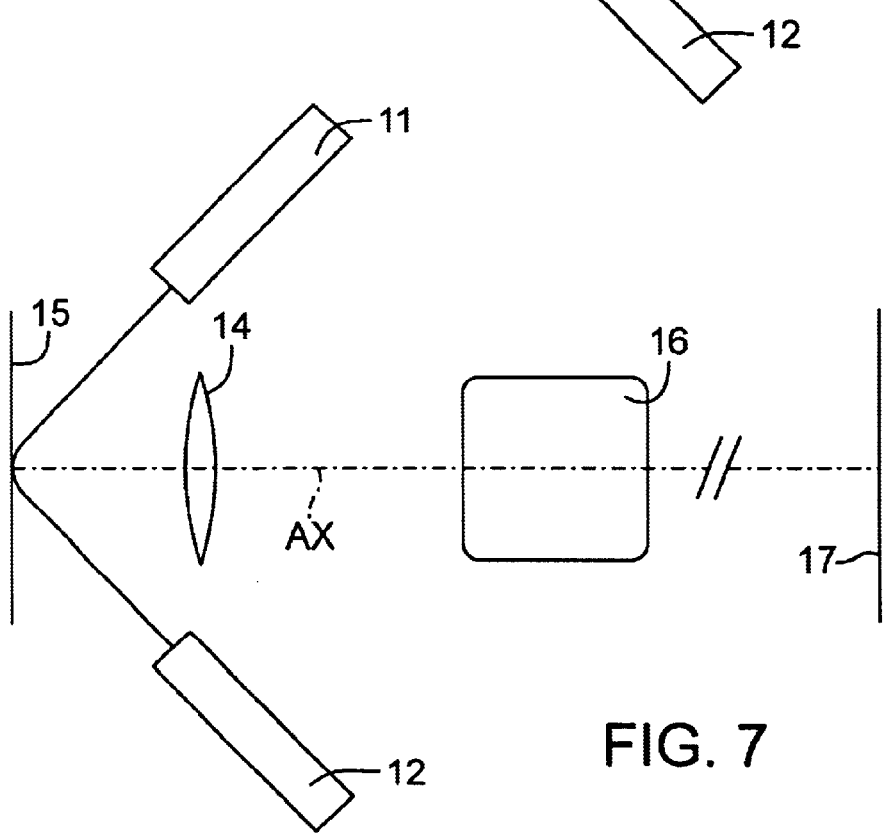
FIG. 7 is a schematic optical diagram of a mapping electron microscope according to a third representative embodiment of the invention.

This embodiment is shown in FIG. 7. Irradiation electrons from the irradiation column 11 and irradiation electrons from the irradiation column 12 are irradiated at respective angles from the optical axis AX of the imaging system. Consequently, the respective electron energies of the various irradiation systems can be changed independently. The respective irradiation-current densities can be varied independently by changing the parameters of the respective electron guns and of the respective irradiation columns. However, with this embodiment, uniform illumination over the entire field is more difficult than with a perpendicular illumination scheme such as those of FIGS. 5 and 6.

In each of the representative embodiments described above, only two irradiation columns 11, 12 are provided. However, greater numbers of irradiation columns can be utilized. Increasing the number of irradiation columns makes it possible (especially when there are numerous types of insulators in or on the specimen surface 15) to impart changes in surface potential for each insulator body by appropriately charging them up.

In addition, although not shown, an effect similar to parallel illumination from the multiple irradiation columns 11, 12 can be obtained using only one irradiation column that produces a beam of which the beam current and incident energy are changed periodically in a repeating manner in serial time segments. This scheme can be utilized because charging is a phenomenon that occurs overlappingly in time and space.

Whereas electron beams are utilized as the irradiating beams in each of the representative embodiments described above, it will be understood that irradiation can be performed with equal facility using another type of charged particle beam such as an ion beam.

Whereas the invention has been described in connection with multiple representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. A mapping electron microscope, comprising:
an irradiation-optical system situated and configured to irradiate simultaneously a common two-dimensional region of a surface of a specimen with a beam of charged particles produced by multiple independently controllable charged-particle sources, so as to cause the region on the specimen surface to emit imaging electrons;
an imaging-electron detector comprising a detection surface; and
an imaging electron-optical system situated and configured to direct the imaging electrons in an image-forming way onto the detection surface, wherein the irradiation-optical system is configured to control, while the region is being irradiated with the beam, a characteristic of the beam such that localized changes in potential due to charging by the beam at one or more locations in the region of the specimen surface, when irradiated by the beam from the irradiation-optical system, are within respective predetermined ranges in which an image of each such respective region can be obtained.

2. The mapping electron microscope of claim 1, wherein the imaging optical system is configured such that each of multiple regions on the specimen surface is irradiated so as to acquire a respective change of surface potential ($U_s$) that is greater than a respective minimum change of surface potential ($U_{min}$) needed to produce a viewable image and a respective maximum change of surface potential ($U_{max}$) beyond which a viewable image cannot be obtained.

3. The mapping electron microscope of claim 1, further comprising a Wien filter situated and configured to direct the beam of charged particles from the irradiation-optical system to the specimen surface.

4. A mapping electron microscope, comprising:
an irradiation-optical system situated and configured to irradiate a common two-dimensional region of a surface of a specimen simultaneously with electrons produced by multiple electron sources, the electrons from each source having a respective current and respective incident energy that are controlled independently at each source, the electrons incident on the specimen surface causing the specimen surface to emit imaging electrons;
an imaging-electron detector comprising a detection surface; and
an imaging electron-optical system situated and configured to route the imaging electrons in an image-forming way to the detection surface of the imaging detector.

5. The mapping electron microscope of claim 4, wherein the irradiation-optical system comprises the multiple electron sources.

6. The mapping electron microscope of claim 4, wherein the irradiation-optical system comprises a separate respective irradiation column corresponding to each electron source.

7. The mapping electron microscope of claim 6, wherein:
each electron source produces a respective irradiation beam; and
the irradiation-optical system comprises a Wien filter situated and configured to receive each irradiation beam from a respective deflection angle relative to an optical axis, and to direct each respective irradiation beam along the optical axis to the specimen surface.

8. The mapping electron microscope of claim 7, wherein:
the irradiation-optical system comprises a first electron source and a second electron source, the first electron source producing a first irradiation beam at an angle $\theta_1$ relative to the optical axis, and the second electron source producing a second irradiation beam at an angle $\theta_2$ relative to the optical axis; and
the respective angles $\theta_1$, $\theta_2$ are established according to:

$$L=(\sin\theta_1/eB)(2m)^{1/2}V_{11}/[(V_{11})^{1/2}+(V_{ret})^{1/2}]$$
$$L=(\sin\theta_2/eB)(2m)^{1/2}V_{12}/[(V_{12})^{1/2}+(V_{ret})^{1/2}]$$

wherein L is a nominal thickness of the Wien filter, B is a magnetic field produced by the Wien filter fulfilling a Wien condition with respect to secondary electrons accelerated from the specimen surface at a retarding voltage ($V_{ret}$), e is the absolute value of an electron's charge, m is the mass of an electron, $V_{11}=V_1+V_{ret}$ wherein $V_1$ is an incident energy of the first irradiation beam, and $V_{12}=V_2+V_{ret}$ wherein $V_2$ is an incident energy of the second irradiation beam.

9. The mapping electron microscope of claim 8, wherein the angles $\theta_1$, $\theta_2$ satisfy the following:

$$\sin\theta_1/\sin\theta_2 = V_{12}[(V_{11})^{1/2}+(V_{ret})^{1/2}]/\{V_{11}[(V_{12})^{1/2}+(V_{ret})^{1/2}]\}.$$

10. The mapping electron microscope of claim 6, wherein:
   each electron source produces a respective irradiation beam; and
   the irradiation-optical system comprises a respective Wien filter for each irradiation beam, each Wien filter being situated and configured to receive the respective irradiation beam from a respective angle relative to an optical axis, and to direct the respective irradiation beam along the optical axis to the specimen surface.

11. A mapping electron microscope, comprising:
   an electron source configured to produce a beam of irradiation electrons, the beam having a first segment containing irradiation electrons at a first independently controllable beam current and incident energy, and a second segment containing irradiation electrons at a second independently controllable beam current and incident energy, the second segment being in temporal series with the first segment, the electrons incident on the specimen surface causing the specimen surface to emit imaging electrons;
   an irradiation-optical system situated and configured to irradiate a surface of a specimen with the beam of irradiation electrons produced by the electron source, the irradiation-optical system being further configured to separate the second segment temporally from the first segment and to control the beam current and incident energy of at least one segment as incident on the specimen surface;
   an imaging-electron detector comprising a detection surface; and
   an imaging electron-optical system situated and configured to route the imaging electrons in an image-forming way to the detection surface of the imaging detector.

12. The mapping electron microscope of claim 11, further comprising a Wien filter situated and configured to direct a beam of charged particles from the irradiation-optical system to the specimen surface.

13. A method for performing mapping-electron microscopy of a surface of a specimen, comprising:
   placing the specimen relative to an irradiation-optical system;
   simultaneously irradiating a common two-dimensional region of the specimen surface with an irradiation charged particle beam passing from a multiple sources through the irradiation-optical system, the irradiation beam causing the irradiated region of the surface to produce imaging electrons;
   directing the imaging electrons through an imaging electron-optical system to an imaging-electron detector in a manner by which the imaging electrons form an image of the irradiated specimen surface on the imaging-electron detector; and
   while irradiating the region of the specimen surface with the irradiation beam, controlling a characteristic of the irradiation beam to achieve an irradiation condition in which localized changes in potential, due to charging by the irradiation beam, at one or more locations in the region of the specimen surface are within respective predetermined ranges in which an image of each such respective region can be obtained.

14. The method of claim 13, wherein each of multiple regions on the specimen surface are irradiated with the irradiation beam so as to exhibit a respective change of surface potential ($U_s$) that is greater than a respective minimum change of surface potential ($U_{min}$) needed to produce a viewable image and a respective maximum charge of surface potential ($U_{max}$) beyond which a viewable image cannot be obtained.

15. A method for performing mapping-electron microscopy of a surface of a specimen, comprising:
   (a) producing multiple respective irradiation electron beams;
   (b) directing the multiple irradiation electron beams simultaneously to irradiate a common two-dimensional region of the specimen surface, while independently controlling a respective beam current and incidence energy of each irradiation electron beam as incident on the specimen surface, the irradiation electron beams incident on the specimen surface causing the irradiated specimen surface to produce imaging electrons; and
   (c) directing the imaging electrons to an imaging-electron detector in a manner by which the imaging electrons form an image of the irradiated specimen surface on the imaging-electron detector.

16. The method of claim 15, wherein:
   step (a) comprises producing a first irradiation electron beam from a first electron source at an angle $\theta_1$ relative to an optical axis, and producing a second irradiation electron beam from a second electron source at an angle $\theta_2$ relative to the optical axis;
   step (b) comprises passing the first and second irradiation electron beams through an irradiation-optical system comprising a Wien filter situated and configured to receive the first and second irradiation electron beams at respective deflection angles relative to the optical axis;
   the respective angles $\theta_1$, $\theta_2$ are established according to:

$$L=(\sin\theta_1/eB)(2m)^{1/2}V_{11}/[(V_{11})^{1/2}+(V_{ret})^{1/2}]$$

$$L=(\sin\theta_2/eB)(2m)^{1/2}V_{12}/[(V_{12})^{1/2}+(V_{ret})^{1/2}]$$

wherein L is a nominal thickness of the Wien filter, B is a magnetic field produced by the Wien filter fulfilling a Wien condition with respect to secondary electrons accelerated from the irradiated specimen surface at a retarding voltage ($V_{ret}$), e is the absolute value of an electron's charge, m is the mass of an electron, $V_{11}=V_1+V_{ret}$ wherein $V_1$ is an incident energy of the first irradiation beam, and $V_{12}=V_2+V_{ret}$ wherein $V_2$ is an incident energy of the second irradiation beam.

17. The method claim 16, wherein the angles $\theta_1$, $\theta_2$ satisfy the following:

$$\sin\theta_1/\sin\theta_2 = V_{12}[(V_{11})^{1/2}+(V_{ret})^{1/2}]/\{V_{11}[(V_{12})^{1/2}+(V_{ret})^{1/2}]\}.$$

* * * * *

UNITED STATES PATENT AND TRADEMARK OFFICE
CERTIFICATE OF CORRECTION

PATENT NO. : 6,717,145 B1
DATED : April 6, 2004
INVENTOR(S) : Takagi et al.

It is certified that error appears in the above-identified patent and that said Letters Patent is hereby corrected as shown below:

Column 2,
Line 57, "electrons-emitted" should be -- electrons emitted --.

Column 4,
Line 4, "$\theta_1, \theta_1, \theta_2$" should be -- $\theta_1, \theta_2$ --.

Column 6,
Line 36, "$U_{min} < U_{s/A} < U_{max}$" should be -- $U_{min} < U_{s/A} < U_{max}$ --.

Line 37, "$U_{min} < U_{s/B} < U_{max}$" should be -- $U_{min} < U_{s/B} < U_{max}$ --.

Line 61, "V and $V_2$" should be -- $V_1$ and $V_2$ --.

Column 7,
Line 20, "$1 = \alpha \cdot FA(V_1 + U_{s/A}) + (1 - \alpha) \cdot FA(V_2 + U_{s/A})$" should be -- $1 = \alpha \cdot FA(V_1 + U_{s/A}) + (1 - \alpha) \cdot FA(V_2 + U_{s/A})$ --.

Line 37, "$1 = \alpha \cdot FC(V_1 + U_{s/C}) + (1 - \alpha) \cdot FC(V_2 + U_{s/C}) \cdot )$" should be -- $1 = \alpha \cdot FC(V_1 + U_{s/C}) + (1 - \alpha) \cdot FC(V_2 + U_{s/C}).)$ --.

Column 8,
Line 47, "$L = (sin\theta_1/eB)(2m)^{1/2} V_{12}/[(V_{12})^{1/2} + (V_{ret})^{1/2}]$" should be -- $L = (sin\theta_2/eB)(2m)^{1/2} V_{12}/[(V_{12})^{1/2} + (V_{ret})^{1/2}]$ --.

Column 12,
Line 14, "respective maximum charge" should be -- respective maximum change --.

Signed and Sealed this

Twenty-third Day of November, 2004

JON W. DUDAS
*Director of the United States Patent and Trademark Office*